(12) United States Patent
Fritz et al.

(10) Patent No.: US 10,677,525 B2
(45) Date of Patent: Jun. 9, 2020

(54) METHOD FOR SEPARATING A HYDROCARBON MIXTURE CONTAINING HYDROGEN, SEPARATING DEVICE, AND OLEFIN PLANT

(71) Applicant: Linde Aktiengesellschaft, München (DE)

(72) Inventors: Helmut Fritz, München (DE); Torben Höfel, München (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 926 days.

(21) Appl. No.: 15/109,960

(22) PCT Filed: Dec. 17, 2014

(86) PCT No.: PCT/EP2014/078168
§ 371 (c)(1),
(2) Date: Jul. 6, 2016

(87) PCT Pub. No.: WO2015/104153
PCT Pub. Date: Jul. 16, 2015

(65) Prior Publication Data
US 2016/0348964 A1  Dec. 1, 2016

(30) Foreign Application Priority Data

Jan. 7, 2014 (EP) .................... 14000040

(51) Int. Cl.
*F25J 3/02* (2006.01)
*C07C 7/04* (2006.01)
(Continued)

(52) U.S. Cl.
CPC ............ *F25J 3/0219* (2013.01); *B01D 3/143* (2013.01); *B01D 53/1487* (2013.01);
(Continued)

(58) Field of Classification Search
CPC .......... F25J 3/0238; F25J 3/0252; F25J 5/002; F25J 5/005; F25J 2200/04; F25J 2200/38;
(Continued)

(56) References Cited

U.S. PATENT DOCUMENTS 3,626,705 A * 12/1971 Knapp .................... F25J 3/062
62/3.1
4,002,042 A * 1/1977 Pryor ........................ C07C 7/04
62/627
(Continued)

FOREIGN PATENT DOCUMENTS

DE  10 2005 003 499 A1  8/2006
DE  10 2005 047 342 A1  4/2007
(Continued)

OTHER PUBLICATIONS

Japanese Patent Application No. 2016-545357 Office Action dated Feb. 26, 2019, with English translation, 4 pages.

*Primary Examiner* — Frantz F Jules
*Assistant Examiner* — Erik Mendoza-Wilkenfel
(74) *Attorney, Agent, or Firm* — Lathrop GPM LLP

(57) ABSTRACT

A method for separating a hydrogen-containing hydrocarbon mixture (C2minus), which in addition to the hydrogen essentially contains hydrocarbons with two carbon atoms and methane, using a distillation column (10). Fluid (a, c, e) of the hydrocarbon mixture (C2minus) is cooled stepwise at a first pressure level, during which time first condensates (b, d) are separated from the fluid (a, c, e). Fluid (e) from the hydrocarbon mixture (C2minus) which remains gaseous after this is fed at the first pressure level into a C2 absorber (7), to which a liquid reflux (r) is added at the top, while a second condensate (f) is drawn off from the sump of the C2 absorber (7) and a gaseous top stream (g) containing predominantly methane and hydrogen is drawn off at the top of the C2 absorber (7). Fluid of the above-mentioned gaseous (Continued)

top stream (g) from the top of the C2 absorber (7) is cooled to a third temperature level and transferred at the first pressure level into a hydrogen separator (8) in which a methane-rich third condensate (i) is separated from the fluid of the gaseous top stream (g), leaving behind a gaseous, hydrogen-rich stream (h). Fluid of the first condensates (b, d) and fluid of the second condensate (f) is depressurized from the first pressure level to a second pressure level below the first pressure level and fed into the distillation column (10) which is operated at the second pressure level. Fluid (e) of the third condensate (i) which is separated in the hydrogen separator (8) from the fluid of the gaseous top stream (g) from the top of the C2 absorber is used as the reflux (r) added at the top of the C2 absorber (7) and transferred from the hydrogen separator to the C2 absorber solely by gravity. The invention also relates to a corresponding separating unit and a corresponding olefin apparatus.

8 Claims, 3 Drawing Sheets

(51) Int. Cl.
  *C07C 7/09* (2006.01)
  *C07C 7/11* (2006.01)
  *B01D 53/00* (2006.01)
  *C10G 70/06* (2006.01)
  *C10G 70/04* (2006.01)
  *B01D 53/14* (2006.01)
  *B01D 3/14* (2006.01)
  *C07C 4/04* (2006.01)

(52) U.S. Cl.
  CPC ............ *B01D 53/1493* (2013.01); *C07C 4/04* (2013.01); *C07C 7/04* (2013.01); *C07C 7/09* (2013.01); *C07C 7/11* (2013.01); *C10G 70/041* (2013.01); *C10G 70/043* (2013.01); *C10G 70/06* (2013.01); *F25J 3/0233* (2013.01); *F25J 3/0238* (2013.01); *F25J 3/0242* (2013.01); *F25J 3/0252* (2013.01); *B01D 53/002* (2013.01); *B01D 53/145* (2013.01); *B01D 2252/205* (2013.01); *B01D 2256/16* (2013.01); *B01D 2256/245* (2013.01); *B01D 2257/702* (2013.01); *F25J 2200/72* (2013.01); *F25J 2200/74* (2013.01); *F25J 2205/02* (2013.01); *F25J 2205/04* (2013.01); *F25J 2210/12* (2013.01); *F25J 2215/60* (2013.01); *F25J 2215/62* (2013.01); *F25J 2235/02* (2013.01); *F25J 2270/02* (2013.01); *F25J 2270/12* (2013.01); *F25J 2270/60* (2013.01); *Y02P 20/51* (2015.11); *Y02P 70/34* (2015.11)

(58) Field of Classification Search
  CPC .. F25J 2200/70; F25J 2200/72; F25J 2200/74; F25J 2200/76; F25J 2200/78; F25J 2240/02; F25J 2205/04; F25J 2205/50; F25J 2215/62; C07C 7/11; C07C 7/04; C07C 7/09; C07C 9/04; C07C 11/04; C10G 70/041; C10G 70/06; B01D 53/002; B01D 53/145
  See application file for complete search history.

(56) References Cited

U.S. PATENT DOCUMENTS

| | | | |
|---|---|---|---|
| 5,685,170 A | 11/1997 | Sorensen | |
| 2005/0198998 A1* | 9/2005 | Lee | ........................ F25J 3/0219 62/612 |
| 2007/0225537 A1 | 9/2007 | Shah | |
| 2010/0217059 A1* | 8/2010 | Reyneke | ................. C07C 4/025 585/651 |
| 2012/0125043 A1* | 5/2012 | Cullinane | ................ B01D 7/02 62/620 |
| 2014/0060113 A1* | 3/2014 | Sapper | ..................... F25J 3/061 62/619 |

FOREIGN PATENT DOCUMENTS

| | | |
|---|---|---|
| DE | 10 2005 050 388 A1 | 4/2007 |
| JP | 2002-333270 A | 11/2002 |

* cited by examiner

METHOD FOR SEPARATING A HYDROCARBON MIXTURE CONTAINING HYDROGEN, SEPARATING DEVICE, AND OLEFIN PLANT

The invention relates to a method for separating a hydrogen-containing hydrocarbon mixture while obtaining a hydrogen-rich stream, a corresponding separating unit and an olefin apparatus with a corresponding separating unit according to the pre-characterising clauses of the independent claims.

PRIOR ART

Methods and apparatus for steam cracking of hydrocarbons are known and are described for example in the article "Ethylene" in Ullmann's Encyclopedia of Industrial Chemistry, online since 15 Apr. 2007, DOI 10.1002/14356007.a10_045.pub2.

By steam cracking, and also using other methods and apparatus, hydrocarbon mixtures are obtained which have to be at least partly separated into their respective components. This can be done in various ways.

The present invention starts, for example, from a separation in which a hydrocarbon stream is produced consisting essentially of hydrocarbons with two carbon atoms, methane and hydrogen. As explained below, a stream of this kind is also referred to as a "C2minus stream". However, the invention is also suitable for other types of separation, as explained hereinafter.

Conventional methods comprise cooling a C2minus stream of this kind stepwise, under pressure, in heat exchangers, and forming a liquid condensate downstream of these heat exchangers. A fraction remaining in gaseous form at a pressure of about 35 bar abs. and at a temperature below about −100° C. is typically fed into a so-called C2 absorber (also known as an "absorber" for short).

This comprises 14 plates, for example, and is operated at about 35 bar and below −100° C.

At the top of the C2 absorber a liquid reflux is added. This is essentially pure methane. In conventional processes it is obtained from a distillation column (so-called demethanizer) into which are fed the condensates separated from the C2minus stream as well as a condensate which is separated off in the sump of the C2 absorber itself.

In the sump of the distillation column, a condensate which consists essentially of hydrocarbons with two hydrocarbons is separated off. A fraction remaining in gaseous form (essentially pure methane) is drawn off at the top of the distillation column and is (partially) liquefied in a top condenser against a refrigerant. Some of the liquefaction product is added to the C2 absorber as the above-mentioned liquid reflux.

As the distillation column is operated at a lower pressure than the C2 absorber, namely at about 28 to 34 or 30 to 32 bar abs., the liquid reflux has to be pressurized in the conventional manner by means of a pump before being fed into the C2 absorber.

Besides olefins and other hydrocarbons, hydrogen is an important product of corresponding apparatus as well, as it can e.g. be used for hydrogenation purposes (e.g. for hydrogenating acetylenes or in hydrotreatment processes in crude oil refineries). Hydrogen can be exported and is, in this case, a product economically at least as attractive as ethylene.

From DE 10 2005 003 499 A1, a method is known in which a C2 absorber, two distillation columns and a reflux container are designed as a single column and are operated at an almost uniform pressure level.

A method of treating a hydrocarbon mixture obtained by steam cracking is also known from DE 10 2005 050 388 A1, a method of recovering propane from natural gas from U.S. Pat. No. 5,685,170 A.

However, it is difficult to operate pumps and expanders for cryogenic media and particular care is required. There is therefore a need for improvements in corresponding methods, wherein, however, a hydrogen-rich stream still should be obtained.

DISCLOSURE OF THE INVENTION

Against this background the invention proposes a method for separating a hydrogen-containing hydrocarbon mixture, a corresponding separating unit and an olefin apparatus with a corresponding separating unit having the features of the independent claims. Preferred embodiments are the subject of the dependent claims and the description that follows.

Before the explanation of the features and advantages of the present invention, their basis and the terminology used will be explained.

The present invention is used particularly for the separation of hydrogen-containing hydrocarbon mixtures which are obtained by steam cracking processes, but is not restricted thereto.

Steam cracking processes are carried out on a commercial scale almost exclusively in tube reactors in which individual reaction tubes (in the form of coiled tubes, so-called coils) or groups of corresponding reaction tubes can also be operated under different cracking conditions. Reaction tubes or sets of reaction tubes operated under identical or comparable cracking conditions and possibly also tube reactors operated under uniform cracking conditions as a whole are also referred to as "cracking furnaces". A steam cracking apparatus (also referred to as an "olefin apparatus") may comprise one or more cracking furnaces.

A so-called "furnace feed" is fed into a cracking furnace and at least partially reacted therein. A large number of hydrocarbons and hydrocarbon mixtures from ethane to gas oil up to a boiling point of typically 600° C. are suitable as furnace feeds. A furnace feed may consist of a so-called "fresh feed", i.e. a feed which is prepared outside the apparatus and is obtained for example from one or more petroleum fractions, petroleum gas and/or petroleum gas condensates. A furnace feed may also consist of one or more so-called "recycle streams", i.e. streams that are produced in the apparatus itself and recycled into a corresponding cracking furnace. A furnace feed may also consist of a mixture of one or more fresh feeds with one or more recycle streams.

A so-called "raw gas" is removed from one or more cracking furnaces and subjected to suitable after-treatment steps. These encompass, first of all, processing of the raw gas, for example by quenching, cooling and drying, so as to obtain a so-called "cracked gas". Occasionally the raw gas is also referred to as cracked gas.

Current methods include in particular the separation of the cracked gas into a number of fractions based on the different boiling points of the components present. In the art, abbreviations are used for these which indicate the carbon number of the hydrocarbons that are predominantly or exclusively contained. Thus, a C1 fraction is a fraction which predominantly or exclusively contains methane (but by convention also contains hydrogen in some cases, and is then also called a "C1minus fraction"). A C2 fraction on the other hand predominantly or exclusively contains ethane, ethylene and/ or acetylene. A C3 fraction predominantly contains propane, propylene, methylacetylene and/or propadiene. A C4 fraction predominantly or exclusively contains butane, butene, butadiene and/or butyne, wherein the respective isomers may be present in different amounts depending on the source of the C4 fraction. The same also applies to a C5 fraction and the higher fractions. Several such fractions may also be combined in one process and/or under one heading. For example, a C2plus fraction predominantly or exclusively contains hydrocarbons with two or more carbon atoms and a C2minus fraction predominantly or exclusively contains hydrocarbons with one or two carbon atoms.

Liquid and gaseous streams may, in the terminology used herein, be rich in or poor in one or more components, "rich" indicating a content of at least 90%, 95%, 99%, 99.5%, 99.9%, 99.99% or 99.999% and "poor" indicating a content of at most 10%, 5%, 1%, 0.1%, 0.01% or 0.001% on a molar, weight or volume basis. Liquid and gaseous streams may also, in the terminology of the art used here, be enriched or depleted in one or more components, these terms also applying to a corresponding content in a starting mixture from which the liquid or gaseous stream was obtained. The liquid or gaseous stream is "enriched" if it contains at least 1.1 times, 1.5 times, 2 times, 5 times, 10 times, 100 times or 1,000 times the amount, "depleted" if it contains at most 0.9 times, 0.5 times, 0.1 times, 0.01 times or 0.001 times the amount of a corresponding component, based on the starting mixture.

A liquid or gaseous stream is "derived" from another liquid or gaseous stream (which is also referred to as the starting stream) if it comprises at least some components that were present in the starting fluid or obtained therefrom. A stream derived in this way may be obtained from the starting stream by separating off or deriving a partial stream or one or more components, concentrating or depleting one or more components, chemically or physically reacting one or more components, heating, cooling, pressurising and the like.

The present application uses the terms "pressure level" and "temperature level" to characterise pressures and temperatures, the intention being to indicate that corresponding pressures and temperatures in a corresponding apparatus do not have to be used in the form of precise pressure or temperature values in order to implement the inventive concept. However, such pressures and temperatures typically vary within certain ranges which are for example ±1%, 5%, 10%, 20% or even 50% either side of a mean value. Corresponding pressure levels and temperature levels may be located in disjointed ranges or in ranges that overlap. In particular, pressure levels will include unavoidable or expected pressure losses caused, for example, by the effects of cooling. The same is true of temperature levels. The pressure levels given in bar are absolute pressures.

A "heat exchanger" is used for the indirect transfer of heat between at least two streams passing for example in countercurrent to one another, for example a warmer, gaseous pressurised stream and one or more colder, liquid streams. A heat exchanger may be formed from a single heat exchanger section or several heat exchanger sections connected in parallel and/or in series, e.g. consisting of one or more blocks of heat exchanger plates. A heat exchanger comprises "passages" which are configured as separate fluid channels with heat exchange surfaces.

A "liquid separator" or "separation vessel" is a container in which a liquid, the so-called condensate, is separated from a gaseous stream or a two-phase stream (which is present partly as a liquid and partly in gaseous form). The condensate may be drawn off at least partly in liquid form from the liquid separator (typically from a lower region, the "sump"), while a fraction remaining in gaseous form may be removed from the liquid separator (typically from an upper region, the "top") at least partly in gaseous form.

A "distillation column" in the terminology used here is a separating unit which is arranged to at least partially separate a mixture of substances (fluid) supplied in gaseous or liquid form or in the form of a two-phase mixture with liquid and gaseous components, optionally also in the supercritical state, i.e. to produce, from the mixture of substances, pure substances or mixtures of substances which are enriched or depleted, or rich or poor, in at least one component compared with the mixture of substances, in the sense described above. Distillation columns are sufficiently known from the field of separation technology. Typically, distillation columns are configured as cylindrical metal containers which are equipped with fittings such as perforated plates or a structured or unstructured packing. A distillation column is characterised inter alia in that a liquid fraction separates off at the bottom, also referred to as the sump. This liquid fraction, which is referred to here as a sump liquid, is heated in a distillation column by means of a sump evaporator so that some of the sump liquid is continuously evaporated and rises in gaseous form within the distillation column. A distillation column is also typically provided with a so-called top condenser into which at least some of a gas mixture concentrating in an upper part of the distillation column or a corresponding pure gas, referred to here as the top gas, is fed, partially liquefied to form a condensate and added at the top of the distillation column as a liquid reflux. Some of the condensate obtained from the top gas can be used elsewhere.

In contrast to a distillation column, an "absorption column" typically does not have a sump evaporator. Absorption columns are also generally known from the field of separation technology. Absorption columns are used for absorption in the phase counterflow and are therefore also referred to as counterflow columns. In counterflow absorption, the releasing gas phase flows upwards through an absorption column. The absorbing solution phase, added at the top and drawn off at the bottom, flows counter to the gas phase. The gas phase is "washed" with the solution phase. In a corresponding absorption column, fittings are also typically provided which ensure a stepwise phase contact (plates, spray zones, rotating plates, etc.) or constant phase contact (unregulated pouring of fillings, packings, etc.). At the top of an absorption column of this kind, a gaseous fluid is obtained which can be drawn off from the column as a "top product". In the sump of the absorption column a liquid is separated off which can be drawn off as a "sump product". In the absorption column the gas phase is depleted of one or more components which go into the sump product. The device referred to as a "C2 absorber", or "absorber", which is used in conventional apparatus for separating a C2minus stream, is also an absorption column. It has the number of bases described above and is operated under the conditions mentioned previously. The absorber is present in addition to a (main) distillation column in which methane, on the one hand, and C2 hydrocarbons (predominantly ethane, ethylene and optionally acetylene), on the other hand, are separated from one another. The C2 absorber serves essentially for the upstream separation of a mixture containing hydrogen and methane.

For the design and specific configuration of distillation columns and absorption columns reference may be made to textbooks on the subject (cf. for example Sattler, K.: Thermische Trennverfahren: Grundlagen, Auslegung, Apparate, [Thermal separation methods: Principles, Design, Apparatus], $3^{rd}$ edition 2001, Weinheim, Wiley-VCH).

Advantages of the Invention

The present invention starts from a known method for separating a mixture of hydrocarbons, which essentially contains hydrocarbons with two carbon atoms as well as methane and also hydrogen. As explained previously, a hydrocarbon mixture of this kind is also known as a C2minus fraction, C2 stream, etc. A method of this kind is carried out, as mentioned previously, using a distillation column in which methane and C2 hydrocarbons are separated from one another. In the method according to the present invention, a hydrogen-rich stream is obtained as well.

In a method of this kind, fluid from the hydrocarbon mixture is cooled stepwise, at a first pressure level, from a first temperature level, via two or more intermediate temperature levels, to a second temperature level. At each of the intermediate temperature levels, condensates are formed from the fluid. These are referred to here as "first condensates".

Where it is stated, within the scope of this application, that "fluid from a stream" or "fluid from a hydrocarbon mixture" is treated in any way, this means that, for example, all the fluid, a fluid derived from a starting fluid, or a partial stream of a stream formed from a corresponding fluid is used. In particular, in the step described previously, a condensate and a fraction remaining in gaseous form are formed from a corresponding fluid. The fraction remaining in gaseous form is cooled down to the next temperature level (an intermediate temperature level or, finally, the second temperature level).

Fluid from the hydrocarbon mixture which remains in gaseous form at the second temperature level, i.e. the fluid from the C2minus hydrocarbon mixture which is not obtained in the form of the first condensates, is fed at the first pressure level into a C2 absorber which is supplied with a liquid reflux at its top. A condensate (referred to here as a "second condensate") is drawn off from the sump of the C2 absorber, and a gaseous top stream is drawn off at the top of the C2 absorber. The latter stream contains predominantly methane and hydrogen. Thus, separation into a condensate and a remaining gaseous fraction is also carried out here.

Fluid from the gaseous top stream from the top of the C2 absorber is cooled to a third temperature level and, likewise at the first pressure level, transferred into a hydrogen separator. The hydrogen separator is another liquid separator, but this one operates at an even lower temperature, in this case a temperature of −150° C., for example. At the stated pressure of 34 to 35 bar and at the temperature mentioned, a liquid, methane-rich fraction is formed at the bottom of the hydrogen separator. A gaseous, hydrogen-rich stream is left at the top which forms one of the products of the method.

According to the invention, the fluid of a condensate which is obtained in the hydrogen separator and which is referred to within the scope of this application as the "third condensate" is used as the reflux added at the top of the C2 absorber.

The present invention thus differs from the prior art inter alia in that the methane-rich third condensate from the sump of the hydrogen separator is used as the reflux in the C2 absorber mentioned above, and not a methane-rich liquid stream which is obtained using a top condenser in the distillation column used. In contrast to the known method, the present invention thus makes it possible to dispense with a pump for transferring a corresponding liquid stream from the distillation column or from its top to the feed point on the C2 absorber. Any pressure difference between the hydrogen separator and the C2 absorber can be overcome by the effects of gravity, by arranging the hydrogen separator at a sufficient height geodetically above the C2 absorber. The third condensate from the hydrogen separator therefore flows down to the C2 absorber purely by gravity and thereby overcomes the pressure difference.

The use of the solution according to the invention hardly changes the material and heat balance of a corresponding system and does not entail any other effects on the process as a whole. The invention makes it possible to reduce the investment costs and simplify the operation of the apparatus. In particular, this relates to the starting up and standby of the reserve pump. Over all there is an increase in the availability of the equipment: pumps and other apparatus and machinery, which can be partly dispensed with according to the present invention, are subject to greater stresses and wear. As a result they are more prone to breakdown than components with no moving parts and therefore fail more frequently or require more maintenance. Occasionally, large parts or areas of the plant have to be shut down because of faults and planned maintenance, with the result that the plant as a whole may become unusable.

Within the scope of the present invention, a so-called "cold pump" for liquid methane, which was conventionally provided, can be omitted altogether. Thus increases the availability and simplifies the operation of an olefin apparatus in which the separating unit according to the invention is incorporated. Moreover, the investment costs are reduced by the savings on a pair of pumps, adjustment is simplified and reduced and a particular column section may be shortened as a result of a reduced hold-up requirement: as is well known, the pumps used for liquid methane, for example, must not run dry and therefore a minimum amount of liquid for pumping must always be provided. This amount, which must typically be sufficient for four to five minutes, is referred to as the "hold-up". In valves, there is less hold-up or none at all, as valves are not damaged in the event of a so-called gas breakthrough.

Thus, in the method according to the invention, the fluid of the third condensate, used as the reflux, is transferred from the hydrogen separator into the C2 absorber solely by the action of gravity. A transfer "solely by the action of gravity" takes place without the use of a pump, with the advantages explained above. In particular, a corresponding hydrogen separator can be incorporated in the top of the C2 absorber used, for example in the form of a liquid sealing plate. In this case, the regulation used can be adapted. A fill level regulation for a corresponding hydrogen separator is replaced in this case by temperature regulation.

In the method according to the invention, fluid of the first condensates and fluid of the second condensate are depressurized from the first pressure level to a second pressure level below the first pressure level and fed into the distillation column which is operated at the second pressure level, while in this distillation column at least one liquid stream consisting essentially of hydrocarbons with two carbon atoms, and one liquid stream consisting essentially of methane, are obtained and drawn off from the distillation column. Because the liquid stream which consists essentially of methane does not have to be pressurised by means of a pump in order to be added as reflux to the C2 absorber, the method according to the invention proves particularly advantageous in this respect.

As mentioned, the distillation column is operated at a second, lower pressure level in the method according to the present invention than the C2 absorber or the hydrogen separator. Therefore, without a corresponding pump, it would not be possible to feed fluid from the top of the distillation column into the C2 absorber. As mentioned at the beginning, the cooling off the feed stream, the operation of the C2 absorber and the operation of the hydrogen separator takes place at about 35 bar, more generally at 30 to 40 bar (the first pressure level) while the distillation column is operated at a lower pressure, namely at about 28 to 34 or 30 to 32 bar (the second pressure level), the second pressure level always being below the first pressure level.

Advantageously, a quantity of the fluid of the third condensate used as reflux is adjusted so as to correspond to a quantity of the liquid stream consisting essentially of methane drawn off from the distillation column. The apparatus can therefore be operated further without any restrictions; the characteristic values do not change.

Advantageously, fluid from the liquid stream drawn off from the distillation column is used at least to cool the fluid of the hydrocarbon mixture from the first temperature level via the intermediate temperature levels to the second temperature level. This enables efficient cooling of the corresponding fluid.

Advantageously, the fluid from the gaseous, hydrogen-rich stream from the hydrogen separator is also used to cool the fluid of the hydrocarbon mixture from the first temperature level via the intermediate temperature levels to the second temperature level and to cool the fluid of the gaseous top stream from the top of the C2 absorber to the third temperature level.

The method according to the invention is particularly suitable for separating a hydrocarbon mixture which is obtained from a cracked gas extracted by means of a steam cracking process.

The invention also relates to a corresponding separating unit. The separating unit is designed to separate a hydrocarbon mixture consisting essentially of hydrocarbons with two carbons as well as methane and hydrogen and comprises a distillation column, a C2 absorber and a hydrogen separator. For the other components of an apparatus of this kind, reference is be made to the explanations provided hereinbefore.

The invention and embodiments of the invention are explained with reference to the appended Figures.

DETAILED DESCRIPTION OF THE DRAWINGS

Figure 1:
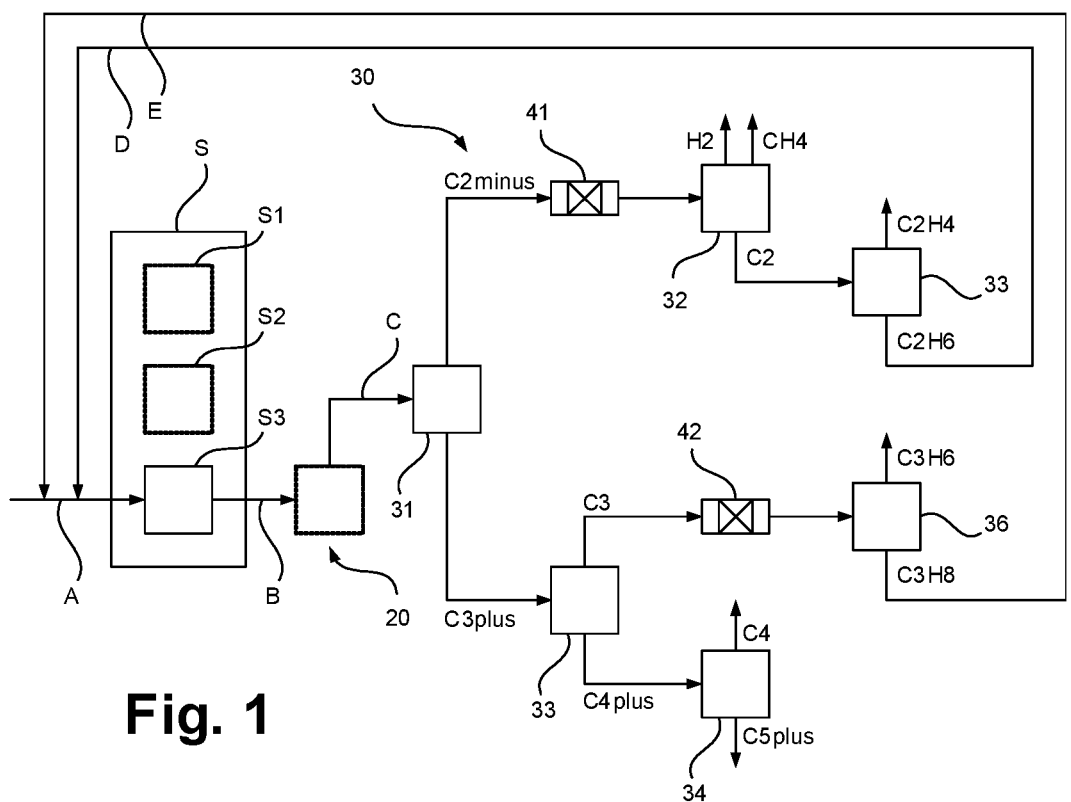
FIG. 1 shows a method for producing hydrocarbons in the form of a schematic flow diagram.

In the Figures, corresponding elements have been given identical reference numerals and are not explained repeatedly, in the interests of clarity.

FIG. 1 shows the course of a method of producing hydrocarbons according to the prior art in the form of a schematic flow diagram. A steam cracking process S is provided which can be carried out using one or more cracking furnaces S1 to S3. Only the operation of the cracking furnace S3 is described hereinafter; the other cracking furnaces S1 and S2 may operate in a corresponding manner or may be omitted.

The cracking furnace S3 is charged with a stream A as the furnace feed, and this may be at least partially a so-called fresh feed which is provided from sources outside the apparatus, and at past partially a so-called recycle stream which is obtained in the method itself, as explained below. The other cracking furnaces S1 and S2 may also be charged with corresponding streams. Different streams may also be fed into different cracking furnaces S1 to S3, one stream may be divided between several cracking furnaces S1 to S3 or several partial streams may be combined to form one combined stream which is fed for example as stream A into one of the cracking furnaces S1 to S3.

As a result of steam cracking in the steam cracking process S a raw gas stream B is obtained which has occasionally is already at this point referred to as a cracked gas stream. The raw gas stream B is treated in a series of treatment stages (not shown) of a treatment process 20, subjected to a so-called oil quench, for example, pre-fractionated, compressed, cooled further and dried.

The correspondingly treated stream B, the actual cracked gas C, is then subjected to a separation process 30. In this process a number of fractions are obtained which, as explained hereinbefore, are named according to the carbon number of the hydrocarbons that they predominantly contain. The separation process 30 shown in FIG. 1 operates according to the principle of "Deethanizer First".

The skilled man will be familiar with numerous other process variants, for example from the article "Ethylene" in Ullmann's Encyclopedia of Industrial Chemistry mentioned hereinbefore, which differ particularly in the preparation of the cracked gas C and/or the separation process used. It is expressly pointed out that the invention can also be used in "Demethanizer First" processes, for example.

In the separation process 30 a C2minus fraction, which may predominantly contain methane, ethane, ethylene and acetylene and, in particular, still hydrogen, is first separated in gaseous form from the cracked gas C in a separating unit 31. The C2minus fraction as a whole is subjected to a hydrotreatment process 41, to convert the acetylene present into ethylene. Then methane CH4 and hydrogen H2 are separated one after the other or together from the C2minus fraction in a C2minus separating unit 32 and used as a fuel gas, for example. The present invention relates particularly to the separating unit 32 which is illustrated in partial schematic view in the following Figures as well.

A C2 fraction remains which is separated in a C2 separating unit 32 into ethylene C2H4 and ethane C2H6. The latter may also be subjected again to the steam cracking process S as a recycle stream D in one or more cracking furnaces S1 to S3. In the embodiment shown the recycle streams D and E are added to the stream A. The recycle streams D and E and the stream A may also be conveyed into different cracking furnaces S1 to S3.

In the separating unit 31 a liquid C3plus fraction remains which is transferred into a separating unit 33 (the so-called depropanizer). In the separating unit 33 a C3 fraction is separated from the C3plus fraction and subjected to a hydrotreatment process 42, in order to react methylacetylene contained in the C3 fraction to form propylene. Then the C3 fraction is separated in a C3 separating unit 34 into propene C3H6 and propane C3H8. The latter may also be subjected again to the steam cracking process S as a recycle stream E in one or more cracking furnaces S1 to S3, separately or with other streams.

In the separating unit 33 a liquid C4plus fraction remains, which is transferred into a fourth separating unit 34 (the so-called debutanizer). In the separating unit 34 a C4 fraction is separated off in gaseous form from the C4plus fraction. A liquid C5plus fraction remains.

It will be understood that all the fractions described can also be subjected to suitable after-treatment steps. For example, 1,3-butadiene may be separated from the C4 fraction. Also, additional recycle streams may be used which may be subjected to the steam cracking process S analogously to the recycle streams D and E.

Figure 2:
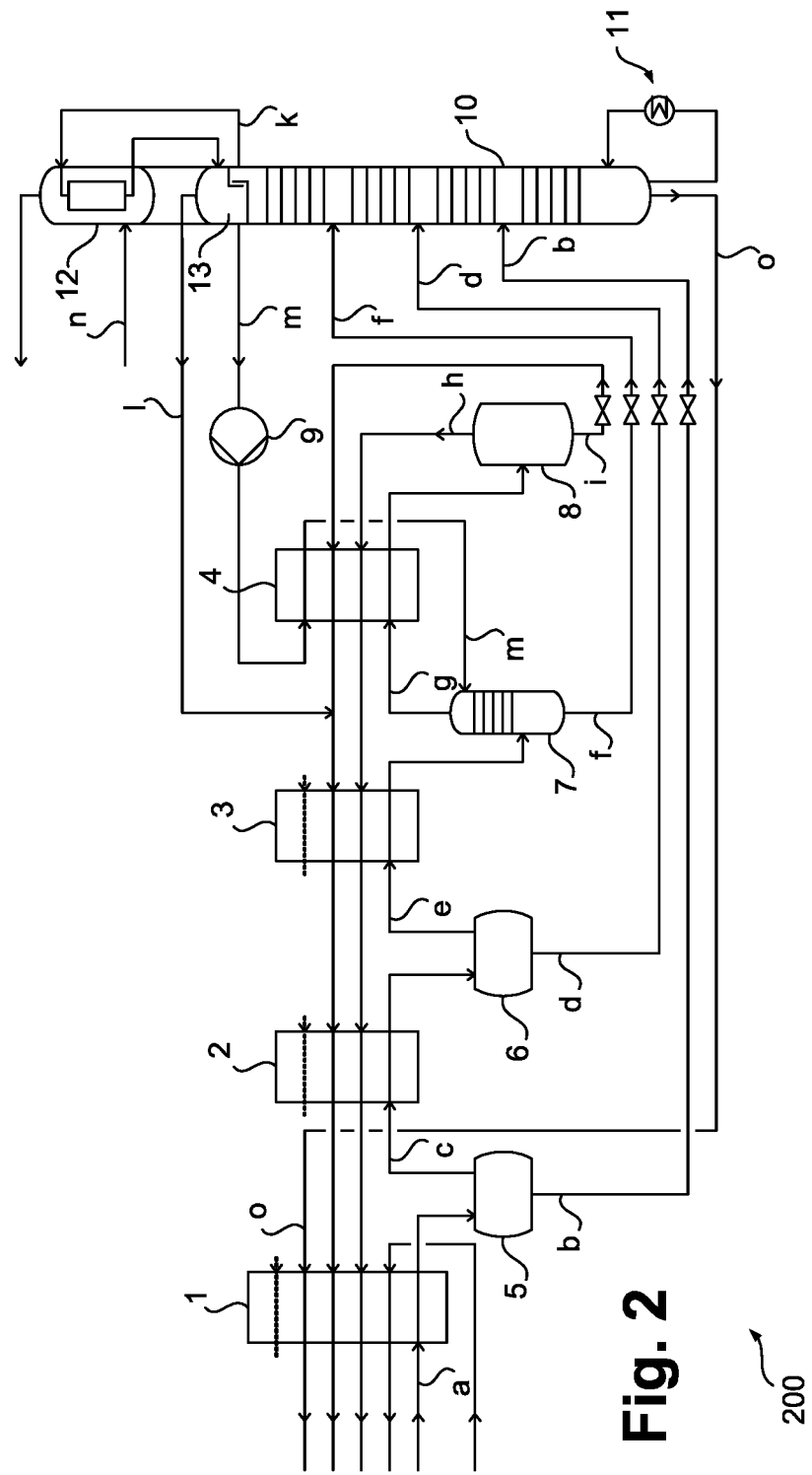
FIG. 2 shows a separating unit for separating a hydrocarbon mixture according to the prior art.

FIG. 2 shows a separating unit for separating a hydrocarbon mixture according to the prior art. The separating unit is generally designated 200 and is designed to separate a hydrocarbon mixture which consists essentially of hydrocarbons with two carbon atoms, methane and hydrogen (i.e. a C2minus fraction). The C2minus fraction is fed into the separating unit 200 in the form of a stream a.

The separating unit 200 comprises a first heat exchanger 1, a second heat exchanger 2, a third heat exchanger 3 and a fourth heat exchanger 4. The stream a is first passed through the first heat exchanger 1 and cooled therein. Then it is fed into a first liquid separator 5. The cooling in the first heat exchanger 1 is carried out so that a liquid condensate is separated off in the first liquid separator 5. This condensate is drawn off at the bottom of the first liquid separator 5 as stream b. The further use of the stream b is described hereinafter.

A fraction of the stream a remaining in gaseous form in the first liquid separator 5 is passed through the second heat exchanger 2 as stream c and then fed into a second liquid separator 6. Here, too, a liquid condensate is separated off at the bottom and is drawn off in the form of the stream d. A fraction of the stream c still remaining in gaseous form is cooled as stream e in the third heat exchanger 3 and fed into a C2 absorber 7. A liquid condensate is also separated off in the sump of the C2 absorber 7 and is drawn off as stream f. In addition, a stream m, the origin of which will be described hereinafter, is added at the top of the C2 absorber 7. A top gas drawn off from the top of the C2 absorber 7 is passed through the fourth heat exchanger 4 in the form of the stream g and then fed into a hydrogen separator 8.

At the bottom of the hydrogen separator 8 a methane-rich condensate is separated off, which is drawn off as the stream i and passed through the fourth to first heat exchangers 4 to 1 in the reverse order and direction. A stream h of a hydrogen-rich top gas from the top of the hydrogen separator 8 is also passed through the fourth to first heat exchangers 4 to 1 in this order and direction.

The drawing is particularly simplified in that it does not show cross-connections between the pipes in which specific streams, for example the streams i and h, are carried. For example, a cross-connection of this kind may make it possible to mix a particular amount of the stream h with the stream i. Nor does the drawing show pipes which are used essentially to start up a corresponding apparatus. For example, in a separating unit 200, it may be envisaged not to add the stream m at the top of the C2 absorber 7 during start-up but to pass it through the fourth to first heat exchangers 4 to 1 in the same way as the stream i.

The separating unit 200 further comprises a distillation column 10 which is operated with a sump evaporator 11 (not described in detail), the heat exchanger of which is operated for example with a propylene stream coming from other parts of the apparatus. The distillation column 10 further comprises a top condenser 12, the operation of which is described hereinafter.

As a result of the successive cooling of the streams a, c and e, the condensates obtained accordingly, which are obtained in the form of the streams b, d and f, contain different amounts of hydrocarbons with two carbon atoms and methane. In particular, the stream f has a higher methane content than the stream d and the stream d has a higher methane content than the stream b.

The streams b, d and f are therefore fed into the distillation column 10 at different heights; the distillation column 10 comprises feed devices suitable for this purpose between the plates, which are shown here in highly diagrammatic form.

From the top of the distillation column 10 a gaseous stream k is drawn off and liquefied in a condensation chamber of the top condenser 12. The liquefied stream is separated into a liquid phase and a gaseous phase in a region 13 at the top of the distillation column 10. The gaseous phase goes into the gas space of the distillation column 10 and combines with more top gas at the top of the distillation column 10. A gaseous stream l can be drawn off from the region 13 and combined with the stream i mentioned previously, downstream of the fourth heat exchanger 4. The stream l predominantly contains methane.

A corresponding liquid methane-rich stream m can also be drawn off from the region 13. The stream m is supplied to the warm end of the fourth heat exchanger 4 by means of a pump 9 (so-called cold pump) and cooled in the fourth heat exchanger 4. Then, as mentioned previously, it is added at the top of the C2 absorber 7. The top condenser 12 of the distillation column 10 can be charged with a stream n from other parts of the apparatus, as refrigerant. This may be an ethylene stream, for example.

In the sump of the distillation column 10, a liquid condensate is separated off, which consists essentially of hydrocarbons with two carbon atoms (and is therefore a so-called C2 fraction). The condensate is drawn off in the form of the stream o, heated in the first heat exchanger 1 and then fed into another separating unit, for example. As mentioned at the beginning, pumps are problematic to operate for cryogenic media such as liquid methane and require greater attention during operation. In the separating unit 200 shown in FIG. 2, this applies particularly to the methane pump 9.

In the separating unit 200 which is shown in FIG. 2, the quantity of the stream m fed in at the top of the C2 absorber is regulated on the basis of a fill level of a corresponding condensate in the region 13 of the distillation column 10. A pressure of the evaporated refrigerant (stream n) in the top condenser 12 is regulated on the basis of a temperature measured in the distillation column 10. The amount of refrigerant fed in the form of the stream n is regulated on the basis of a fill level in the top condenser 12.

Figure 3:
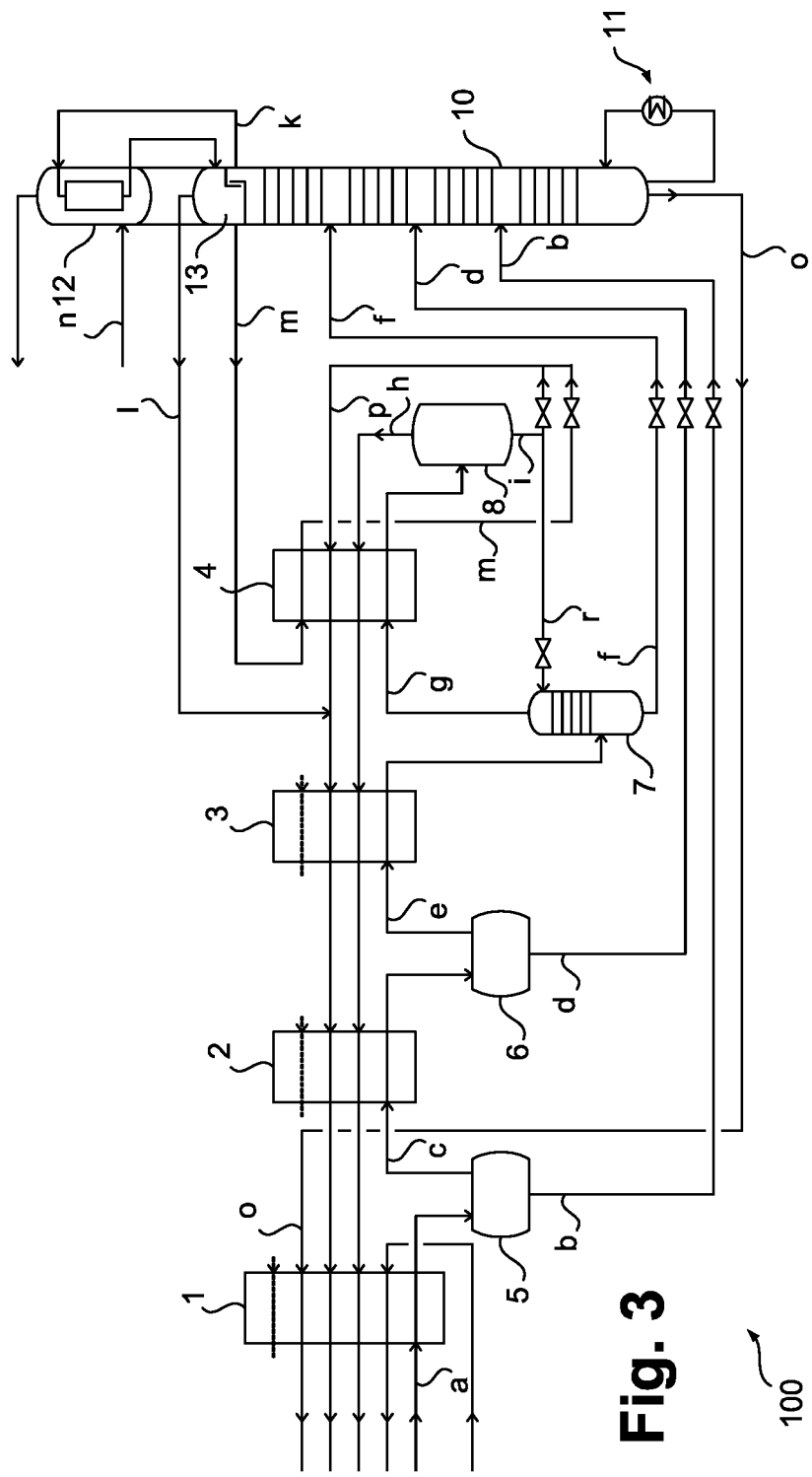
FIG. 3 shows a separating unit for separating a hydrocarbon mixture according to an embodiment of the invention.

FIG. 3 shows a separating unit 100 according to one embodiment of the invention. The separating unit 100 comprises the essential components of the separating unit 200 shown in FIG. 2. These will not be described again.

However, in contrast to the separating unit 100 shown in FIG. 2, the pump 9 is omitted here. Moreover, the stream n is not added at the top of the C2 absorber 7 but combined with the stream i from the sump of the methane separator 8 to form a stream p. The stream p, instead of only the stream i as before, is passed through the fourth to first heat exchangers 4 to 1 in the order described previously.

However, before it is combined with the stream m, a partial stream r is branched off from the stream i, in particular, and added at the top of the C2 absorber 7 instead of the stream m (cf. separating unit 200 of FIG. 2). If, as schematically shown in FIG. 3, at least the feed point for the stream l into the C2 absorber 7 is arranged below a removal point for the stream i from the hydrogen separator 8, condensate occurring in the hydrogen separator 8 can be passed as a reflux in a restricted flow through a corresponding valve (not given a reference numeral) onto the C2 absorber by the effect of gravity. The quantity of the condensate from the hydrogen separator 8 added to the top of the C2 absorber in the form of the stream r advantageously corresponds to the quantity of methane drawn off from the distillation column 10 in the form of the stream m and is replaced by it in order to generate cold in the fourth heat exchanger 4. As only a low pressure level is needed for correspondingly supplying the fourth heat exchanger 4, the methane pump 9 can be omitted.

The invention claimed is:

1. Method for separating a hydrogen-containing hydrocarbon mixture (C2minus), which in addition to the hydrogen essentially contains hydrocarbons with two carbon atoms and methane, using a distillation column (10), wherein the hydrocarbon mixture (C2minus) or a part of the hydrocarbon mixture (C2minus) is cooled stepwise, at a first pressure level, from a first temperature level, via two or more intermediate temperature levels, to a second temperature level, first condensates (b, d) being separated from the hydrocarbon mixture (C2minus) or said part of the hydrocarbon mixture (C2minus) at each of the intermediate temperature levels, a part of the hydrocarbon mixture (C2minus) or said part of the hydrocarbon mixture (C2minus) which remains gaseous at the second temperature level and which is not obtained in the form of the first condensates (b, d) is fed at the first pressure level into a C2 absorber (7), to which a liquid reflux (r) is added at a top, wherein a second condensate (f) is drawn off from a sump of the C2 absorber (7) and a gaseous top stream (g) comprising predominantly methane and hydrogen is drawn off at the top of the C2 absorber (7), the gaseous top stream (g) from the top of the C2 absorber (7) or a part of the gaseous top stream (g) is cooled to a third temperature level and transferred at the first pressure level into a hydrogen separator (8) in which a methane-rich third condensate (i) is separated from the gaseous top stream (g) or said part of the gaseous top stream (g), leaving behind a gaseous, hydrogen-rich stream (h), and the first condensates (b, d) or a part of the first condensates (b, d) and the second condensate (f) or a part of the second condensate (f) is depressurized from the first pressure level to a second pressure level below the first pressure level and fed into the distillation column (10) which is operated at the second pressure level, wherein in the distillation column (10) at least a liquid stream (o) essentially consisting of hydrocarbons with two carbon atoms, and a liquid stream (m) essentially consisting of methane are obtained and drawn off from the distillation column (10), characterised in that the reflux (r) added at the top of the C2 absorber is formed from fluid of the methane-rich third condensate (i) which is separated in the hydrogen separator (8) from the gaseous top stream (g) from the top of the C2 absorber (7) and transferred from the hydrogen separator (8) into the C2 absorber (7) solely by the effect of gravity, wherein the C2 absorber is an absorption column not comprising a sump evaporator or an absorption column comprising a sump evaporator which is not operated, and the C2 absorber comprises installments provided for a stepwise or a constant phase contact.

2. The method according to claim 1, wherein a quantity of the fluid of the third condensate (i) used as reflux (r) is selected so as to be approximately equivalent to a quantity of the liquid stream (m), consisting essentially of methane, which is drawn off from the distillation column (10).

3. The method according to claim 1, wherein fluid from the liquid stream (m) which is drawn off from the distillation column (10) is used at least to cool the fluid (a, c, e) of the hydrocarbon mixture (C2minus) from the first temperature level, via the intermediate temperature levels, to the second temperature level.

4. The method according to claim 1, wherein fluid from the gaseous, hydrogen-rich stream (h) from the hydrogen separator (8) is used to cool the fluid (a, c, e) of the hydrocarbon mixture (C2minus) from the first temperature level, via the intermediate temperature levels, to the second temperature level, and to cool the fluid of the gaseous top stream (g) from the top of the C2 absorber (7) to the third temperature level.

5. The method according to claim 1, wherein the hydrocarbon mixture (C2minus) is obtained from a cracked gas obtained by means of a steam cracking process (50).

6. Separating unit (100) which is designed to separate a hydrogen-containing hydrocarbon mixture (C2minus), which in addition to hydrogen essentially contains hydrocarbons with two carbon atoms and methane, and comprises at least one distillation column (10), a C2 absorber (7) and a hydrogen separator (8), as well as a steam cracking process designed to cool the hydrocarbon mixture (C2minus) or a part of the hydrocarbon mixture (C2minus), at a first pressure level, stepwise from a first temperature level, via two or more intermediate temperature levels, to a second temperature level and to separate first condensates (b, d) from the hydrocarbon mixture (C2minus) or said part of the hydrocarbon mixture (C2minus) at each of the intermediate temperature levels, to feed, at the first pressure level, a part of the hydrocarbon mixture (C2minus) or said part of the hydrocarbon mixture (C2minus) which remains gaseous at the second temperature level and which is not obtained in the form of the first condensates (b, d) into the C2 absorber (7), to add a liquid reflux (r) to the C2 absorber at a top, and to draw off a second condensate (f) from a sump of the C2 absorber (7) and a gaseous top stream (g), predominantly containing methane and hydrogen, at the top of the C2 absorber (7), to cool the gaseous top stream (g) from the top of the C2 absorber (7) or a part of the gaseous top stream (g) to a third temperature level and transfer the gaseous top stream (g) or said part of the gaseous top stream (g), at the first pressure level, into the hydrogen separator (8) and therein to separate off a methane-rich third condensate (i) from the gaseous top stream (g) or said part of the gaseous top stream (g), leaving behind a gaseous, hydrogen-rich stream (h), and to depressurize the first condensates (b, d) or a part of the first condensates (b, d) and the second condensate (f) or a part of the second condensate (f) from the first pressure level to a second pressure level below the first pressure level and to fed it into the distillation column (10), to operate the distillation column (10) at the second pressure level, and to obtain in, and to draw off from, the distillation column (10) at least a liquid stream (o) essentially consisting of hydrocarbons with two carbon atoms, and a liquid stream (m) essentially consisting of methane, characterised in that fluid communication is provided which is designed to form the reflux (r) added at the top of the C2 absorber from fluid (e) of the methane-rich third condensate (i) which is separated in the hydrogen separator (8) from the gaseous top stream (g) from the top of the C2 absorber (7) and is transferred from the hydrogen separator (8) into the C2 absorber (7) solely by the effect of gravity wherein the C2 absorber is an absorption column not comprising a sump evaporator or an absorption column comprising a sump evaporator which is not operated, and the C2 absorber comprises installments provided for a stepwise or a constant phase contact.

7. The separating unit (100) according to claim 6, which is designed for carrying out the method according to claim 1.

8. Olefin apparatus which is designed to carry out a steam cracking process (50) using at least one cracking furnace (51-53), wherein the steam cracking process (50) is designed to recover a hydrocarbon mixture (C2minus) consisting essentially of hydrocarbons with two carbon atoms as well as methane and hydrogen, from fluid of a cracked gas (C) of the at least one steam cracking process (50), characterised by at least one separating unit (100) according to claim 6, which is designed to separate the hydrocarbon mixture (C2minus).

* * * * *